United States Patent [19]
Fox

[11] 3,964,474
[45] June 22, 1976

[54] UNIVERSAL CERVICAL COLLAR

[76] Inventor: J. DeWitt Fox, 1894 Carla Ridge, Beverly Hills, Calif. 90210

[22] Filed: May 27, 1975

[21] Appl. No.: 580,926

[52] U.S. Cl. .......................... 128/87 B; 128/DIG. 23
[51] Int. Cl.² ............................................ A61F 5/04
[58] Field of Search ............ 128/68, DIG. 23, 87 B, 128/87 R, 75

[56] References Cited
UNITED STATES PATENTS

| | | | |
|---|---|---|---|
| 2,284,058 | 5/1942 | Kaiser et al. ................. | 128/DIG. 23 |
| 3,320,950 | 5/1967 | McElvenny ........................... | 128/75 |
| 3,374,785 | 3/1968 | Gaylord ................................. | 128/75 |
| 3,850,164 | 11/1974 | Hare ........................... | 128/DIG. 23 |

*Primary Examiner*—Lawrence W. Trapp
*Attorney, Agent, or Firm*—Ralph B. Pastoriza

[57] ABSTRACT

A cervical collar is made of plastic foam and includes a thin band of resilient plastic material biasing the foam into an annular shape terminating in opposed rear ends which may be separated to circumferentially expand the collar against the bias of the band for fitting about a patient's neck. A front central top portion of the collar includes a depression and the top surface itself is beveled and shaped in such a manner as to comfortably cradle a patient's front jaw portion and side areas of the head. An outer covering of fabric material may be applied about the collar for purposes of cleanliness and enhancement of the aesthetic appearance of the collar.

7 Claims, 4 Drawing Figures

UNIVERSAL CERVICAL COLLAR

This invention relates to cervical collars worn by patients to relieve and aid in curing neck injuries and more particularly to a uniquely shaped collar making it universal in use.

BACKGROUND OF THE INVENTION

Cervical collars are worn by patients who have suffered neck injuries to aid the patient in holding his head relatively stationary. By minimizing the tendency of a person to turn or twist his neck, the injury will heal in a shorter time than would be the case in the absence of such support.

Known cervical collars generally include a soft pliable foam material incorporating a curved metal band buried within the material to hold it in an annular configuration and exert a bias force when the rear opposed ends of the collar are separated to fit the same about the patient's neck. Generally the collars are of fairly uniform cross section throughout their annular configuration the same being somewhat similar to a short cylindrical or tubular section.

Since patients have different neck lengths, it is not uncommon practice to provide the collars of varying axial extent so that the patient's lower jaw and side head portions will be properly supported. This requirement of providing different sized collars has disadvantages in that only a certain sized collar will fit certain patients. In other words, any given collar available in the prior art is not really universal.

Other problems associated with available cervical collars relate to the general discomfort of a patient because of the uniform cross sectional shaping of the collar itself. Proper cradling of the lower jaw and the side areas of the head is thus lacking to a large degree. Further, the available collars tend to become dirty with use and their normally bland white color renders them conspicuous on a patient and not particularly attractive from an aesthetic standpoint.

BRIEF DESCRIPTION OF THE PRESENT INVENTION

Bearing the foregoing considerations in mind, the present invention contemplates a vastly improved cervical collar which is primarily distinguished in that it is so designed as to be univeral in use so that it will serve patients with both short and long necks. Further, the collar of the present invention avoids the use of metal springs embedded within the foam material forming the collar and thus renders the manufacture of the collar less expensive and more simple than those types which incorporate such a spring.

Briefly, the cervical collar itself in accord with the present invention comprises a plastic foam member curved into an annular shape with its ends terminating in the rear in spaced opposed relationship. At least one band of resilient plastic material different from the plastic foam is biased into a desired annular shape with its ends terminating in spaced opposed relationship. This band is secured preferably to the inside but optionally to the outside of the foam member to hold the foam member in its annular configuration. The annular configuration is circumferentially expandable against the bias of the band by increasing the separation space of its ends so that the foam member may be fitted snugly about a person's neck. A further feature of this invention resides in the provision of a front depression in the upper front portion of the plastic foam member for receiving and comfortably cradling the forward under portion of a person's jaw.

Further features include beveling of the top surface of the plastic member and forwardly sloping the same from its side portions towards the front depression so that the extended portions of a patient's jaw towards his ears are carefully supported and cradled by the collar regardless of the length of the patient's neck.

A further feature includes the provision of a stretchable fabric covering which may be easily slipped over the collar to not only keep it clean but render it aesthetically attractive.

BRIEF DESCRIPTION OF THE DRAWINGS

A better understanding of this invention will be had by referring to the accompanying drawings in which.

DETAILED DESCRIPTION OF THE PREFERRED EMBODIMENT

Figure 1:
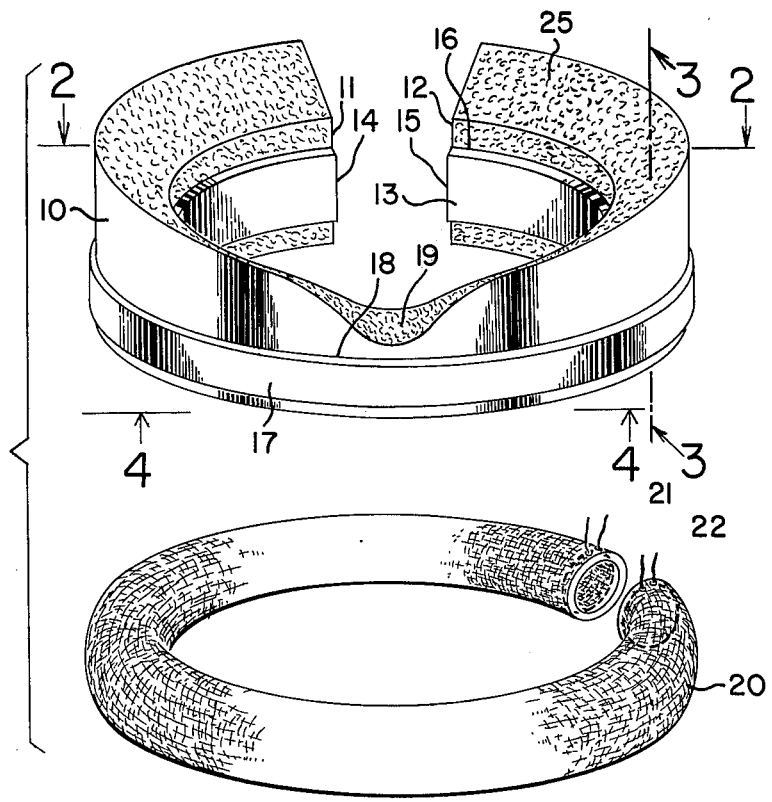
FIG. 1 is a front perspective view of the collar of this invention showing in exploded relationship a stretchable fabric covering which may be disposed over the collar.

Referring first to FIG. 1 the cervical collar includes a plastic foam member 10 curved into an annular shape with its ends 11 and 12 terminating in the rear in spaced opposed relationship. The plastic foam may constitute styrofoam or equivalent resilient plastic foam material.

As shown, at least one band 13 of resilient plastic material different from the plastic foam is biased into a desired annular shape with its ends 14 and 15 terminating in the spaced opposed relationship. This band is secured to the inside surface of the foam member as at 16 and will hold the foam member in its annular configuration, this annular configuration being circumferentially expandable against the bias of the band by increasing the separation space of its ends so that the foam member will fit snugly about a person's neck. The band 13 constitutes a plastic such as acrylic which will have a memory when flexed from its formed configuration; that is, if the plastic band is circumferentially expanded, it will return to its annular formed configuration.

An additional band of resilient plastic material is shown at 17 secured to and disposed about the outside surface of the plastic foam member 10 as indicated at 18. This band may be of the same material as the band 13 and will provide a biasing force when the rear ends of the collar are separated to circumferentially expand the plastic foam member.

The band 17 is shown merely to illustrate that such biasing band may be utilized on the outside rather than the inside or, alternatively, both bands may be used.

Still referring to FIG. 1, it will be noted that the upper front portion of the plastic foam member 10 includes a front depression 19. This depression is shaped for receiving and comfortably cradling the forward under portion of a patient's jaw.

Shown disposed below the collar in FIG. 1 is a sock-like stretchable fabric material 20 formed into an annular or toroidal shape and terminating in at least one open end which may be closed as by a simple draw string 21. In the example shown, both ends of the sock 20 are open, there being provided draw strings 22 for the other end. The fabric material is stretchable in such a manner that it may be slipped over one of the ends 11 or 12 of the plastic foam member 10 of FIG. 1 to completely cover the collar, the draw strings 21 and 22 then being pulled to close off the ends of the fabric.

Because the fabric material is stretchable, it will conform to the exterior shape of the collar. Further, the fabric material may be provided with an aesthetically pleasing design of a suitable pattern to match the patient's clothing. In this respect, it will be understood that several such sock-like coverings in different patterns may be provided for use by the patient.

A further advantage of the fabric covering is that it will maintain the collar itself in a clean condition, the cover itself being easily removable for washing.

Figure 2:
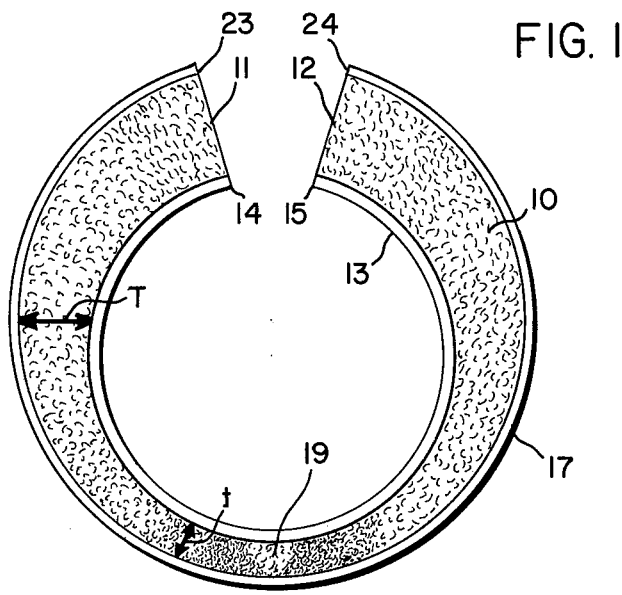
FIG. 2 is a top plan view looking in the direction of the arrows 2—2 of FIG. 1.

Referring now to FIG. 2 further details of the collar structure will become evident. As shown, the additional plastic band 17 encircling the outside surface of the collar 10 terminates in rear ends 23 and 24 flush with the ends 11 and 12 of the plastic foam member itself. The thickness of the plastic foam member gradually decreases from the sides towards the front. Thus, there is designated by the letter T the thickness of the foam at the side portion and by the small letter $t$ the thickness of the foam at the front portion. By gradually decreasing the thickness as illustrated, there is provided greater resiliency in the front area of the collar to accommodate emergency head movement but still tend to hold the patient's head in a straightforward position under normal use. In this respect, the depression 19 cooperates to inhibit the patient's turning or twisting his head while wearing the collar.

Figure 3:
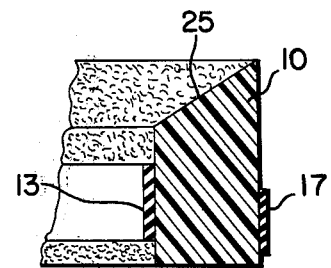
FIG. 3 is a fragmentary cross section taken in the direction of the arrows 3—3 of FIG. 1; and, FIG. 4 is a front elevational view looking in the direction of the arrows 4—4 of FIG.1.

Referring to the cross section of FIG. 3, it will be noted that the top surface 25 of the plastic foam member 10 is beveled radially inwardly and downwardly. As a consequence, there is a variation in the vertical distance from the top to the bottom of the collar as measured from its outside and inside. Persons with long necks will thus have the lower sides of their head and jaw supported towards the outside portion of the top surface 25 whereas those patients with shorter necks will have the same areas cradled by the inside portion of the top surface thus rendering the collar essentially universal in use.

Figure 4:
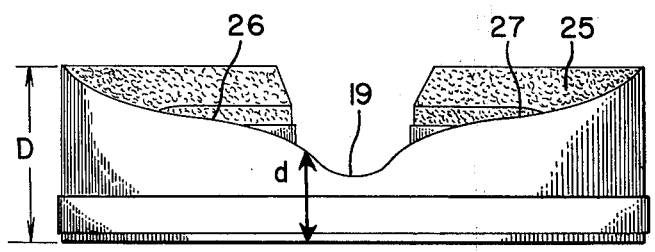

Referring finally to FIG. 4, it will be further noted that the top surface 25 slopes downwardly from opposite sides towards the front depression 19 as indicated at 26 and 27. This particular shaping of the top surface results in a very comfortable cradling of the rearward extended portions of a patient's jaw towards his ears. In FIG. 4 the vertical distance at the side is designated by the letter D and at the front portion by the small letter $d$.

From the foregoing description, it will be evident that the present invention has provided a greatly improved universal type cervical collar which overcomes many of the problems associated with prior art collars all as described heretofore.

What is claimed is:

1. A cervical collar comprising, in combination:
    a. a plastic foam member curved into an annular shape with its ends terminating in the rear in spaced opposed relationship; and,
    b. at least one band of resilient plastic material different from said plastic foam biased into a desired annular shape with its ends terminating in spaced opposed relationship secured to said foam member to hold the foam member in its annular configuration, said annular configuration being circumferentially expandable against the bias of said band by increasing the separation space of its ends so that the foam member will fit snugly about a person's neck, the upper front portion of said member including a front depression for receiving and comfortably cradling the forward under portion of a patient's jaw.

2. A collar according to claim 1, in which said band is secured to and disposed about the inside surface of said plastic foam member.

3. A collar according to claim 2, including an additional band of resilient plastic material different from said plastic foam biased into an annular shape larger than the annular shape of said first mentioned band with its ends in spaced opposed relationship and secured to and disposed about the outside surface of said plastic foam member, said member being circumferentially expandable against the bias of both of said bands.

4. A collar according to claim 1, in which said band is secured to and disposed about the outside surface of said plastic foam member.

5. A collar according to claim 1, in which the top surface of said plastic foam member is beveled radially inwardly and downwardly with its top surface sloping downwardly from opposite side portions toward said front depression so that the vertical distance between the top and bottom surfaces of the collar decreases from the sides towards the front whereby rearward extended portions of a patient's jaw towards his ears are cradled by the top surface of said collar and such cradling takes place for patients with both short and long necks so that the collar is universal in use.

6. A collar according to claim 5, in which the thickness of said plastic foam member gradually decreases from the sides towards the front so as to provide greater resiliency in the front area to accommodate emergency head movement but still tend to hold the patient's head in a straightforward position under normal use.

7. A cervical collar according to claim 1, including a removable sock like stretchable fabric material arranged to be fitted over one of the rear ends of said plastic foam member to completely enclose the member, said fabric material being of a color and design to enhance the aesthetic appearance of said collar and being removable for washing and replaceable on said collar.

\* \* \* \* \*